United States Patent
Huber et al.

(10) Patent No.: US 10,183,904 B2
(45) Date of Patent: Jan. 22, 2019

(54) PRODUCTION OF 1,5-PENTANEDIOL VIA UPGRADING OF TETRAHYDROFUFURYL ALCOHOL

(71) Applicant: Wisconsin Alumni Research Foundation, Madison, WI (US)

(72) Inventors: George Willis Huber, Middleton, WI (US); James A. Dumesic, Verona, WI (US); Kevin J. Barnett, Madison, WI (US); Zach J. Brentzel, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 392 days.

(21) Appl. No.: 15/004,091

(22) Filed: Jan. 22, 2016

(65) Prior Publication Data
US 2017/0210688 A1    Jul. 27, 2017

(51) Int. Cl.
C07C 31/20    (2006.01)
C07C 29/132   (2006.01)

(52) U.S. Cl.
CPC .................................. *C07C 29/132* (2013.01)

(58) Field of Classification Search
CPC .................................................... C07C 29/132
USPC ........................................................ 568/861
See application file for complete search history.

(56) References Cited

U.S. PATENT DOCUMENTS 3,806,551 A * 4/1974 Blume .................. C08F 36/00
526/72

OTHER PUBLICATIONS

Schniepp et al., "Preparation of Dihydropyran, 5-Hydroxyvaleraldehyde and 1,5-Pentanediol from Tetrahydrofurfuryl Alcohol." J. Amer. Chem. Soc., Aug. 1946, 68(8): 1646-1648. (Year: 1946).*
Koso et al.; Chemoselective hydrogenolysis of tetrahydrofurfuryll alcohol to 1,5-pentanediol; Chem. Comm; 2009; 2035-2037; (Year: 2009).*
Koso et al.; Chemoselective hydrogenolysis of tetrahydrofurfuryl alcohol to 1,5-pentanediol; Chem. Comm; 2009; 2035-2037; UK.
Bardin et al., (1998) Acidity of Keggin-type Heteropolycompounds Evaluated by Catalytic Probe Reactions, Sorption Microcalorimetry and Density Functional Quantum Chemical Calculations, *J. of Physical Chemistry B*, 102:10817-10825.
Schniepp and Geller (Aug. 1946), "Preparation of Dihydropyran, δ-Hydroxyvaleraldehyde and 1,5-Pentanediol from Tetrahydrofurfuryl Alcohol." *J. Amer. Chem. Soc.*, 68(8):1646-1648.

* cited by examiner

*Primary Examiner* — Deborah D Carr
(74) *Attorney, Agent, or Firm* — Joseph T. Leone, Esq.; DeWitt Ross & Stevens S.C.

(57) ABSTRACT

A method of making 1,5-pentanediol from tetrahydrofurfural alcohol. The method includes the steps of dehydrating tetrahydrofurfural alcohol (THFA) to dihydropyran (DHP); hydrating at least a portion of the DHP to 2-hydroxytetrahydropyran (2-HY-THP) in the absence of homogeneous acid; and hydrogenating at least a portion of the 2-HY-THP to 1,5-pentanediol. The method can be conducted entirely in the absence of noble metal catalysts.

18 Claims, 9 Drawing Sheets

PRODUCTION OF 1,5-PENTANEDIOL VIA UPGRADING OF TETRAHYDROFUFURYL ALCOHOL

FEDERAL FUNDING STATEMENT

This invention was made with government support under DE-EE0006878 awarded by the US Department of Energy and EEC0813570 awarded by the National Science Foundation. The government has certain rights in the invention.

BACKGROUND

There is currently a growing interest in renewable, biochemical production of value-added chemicals from biomass. Among these chemicals are α,ω-diols. These terminal diols are particularly attractive because of the high market prices they command, currently >$2,700/MT (2015 US dollars). 1,5-Pentanediol (1,5-PD) is particularly attractive because it is not currently produced in large quantities from petroleum feedstocks. 1,5-PD is used as a plasticizer and is also used as a precursor in the manufacture of polyurethanes. In recent academic literature, 1,5-PD is made via direct hydrogenation of furfural and subsequent hydrogenolysis of tetrahydrofurfural alcohol:

This conventional route has relatively low selectivity and low conversion to 1,5-PD and must run at a relatively high temperature (~250° C. or greater) when employing base-metal catalysts. The necessity of noble metal catalysts renders the conventional route economically infeasible.

Interest in more efficient routes to 1,5-PD is not new. For example, Schniepp and Geller (August 1946) *J. Amer. Chem. Soc.* 68(8):1646-1648, describe a route to 1,5-PD in which tetrahydrofurfural alcohol is converted in the presence of activated alumina to dihydropyran (DHP). The DHP is then hydrated with a homogeneous acid catalyst (0.2 N HCl) to yield a mixture that was approximately 84 wt % gamma-hydroxyvaleraldehyde (i.e., 5-hydroxypentanal) and 16 wt % 2-hydroxytetrahydropyran. The reaction mixture is neutralized with base (0.4 N NaOH). Notably, the two intermediates in the mixture were separated via reduced pressure distillation. The last step is performed solely on the 5-hydroxypentanal, which is reduced (hydrogenated) to 1,5-PD. Overall yield of 1,5-PD when the 5-hydroxypentanal and 2-hydroxytetrahydropyran were separated prior to the final step was 70% from tetrahydrofurfural alcohol. However, without the intermediate isolation of the 5-hydroxypentanal, overall yield of 1,5-PD dropped to 60-62%. In both instances, the intermediate was subjected to acid hydrolysis with HCl.

SUMMARY

Disclosed herein is a method to produce 1,5-PD from tetrahydrofurfural alcohol (THFA). In a first step THFA is dehydrated using a metal-oxide catalyst, such as γ-Al$_2$O$_3$ ($1/kg), to yield dihydropyran (DHP). The DHP is then hydrated in water at low temperatures (e.g., about 70° C. to about 100° C.), preferably in the absence of catalysts and in the absence of added homogenous acid, to yield 2-hydroxytetrahydropyran (2-HY-THP). 2-HY-THP is a highly reactive alternative (as compared to THFA) for a subsequent hydrogenolysis reaction step in which the 2-HY-THP is ring-opened to yield 1,5-PD. This can be accomplished using a number of different metallic catalysts. Preferred both on cost and performance grounds is a Co/TiO2 monometallic catalyst or a NiMo/C bimetallic catalyst. The ring-opening reaction of 2-HY-THP occurs at rates that are about 100-fold faster than the corresponding reaction with THFA. The ring-opening reaction of 2-HY-THP can be catalyzed using relatively inexpensive base metal catalysts (rather than very expensive noble metal catalysts).

The entire method requires only inexpensive metal-oxide and base metal catalysts. These catalysts are several orders of magnitude cheaper than the expensive noble metal catalysts used in the conventional method to produce 1,5-PD. The method can also be carried out at relatively mild reaction conditions, without the need of added homogenous acid (and thus without the need to neutralize any acid). The method also incurs far lower separation costs. The method results in >90% overall yields to 1,5-PD (based on THFA).

Disclosed herein is a method of making 1,5-pentanediol. The method comprises dehydrating tetrahydrofurfural alcohol (THFA) to dihydropyran (DHP), hydrating at least a portion of the DHP to 2-hydroxy-tetrahydropyran (2-HY-THP) in the absence of homogeneous acid, and hydrogenating at least a portion of the 2-HY-THP to 1,5-pentanediol.

The THFA can be dehydrated by contacting it with a solid acid catalyst, such as a solid Brønsted acid catalyst, a solid Lewis acid catalyst, and combinations thereof. The dehydration step may be conducted on neat THFA or on an aqueous solution of THFA in which the THFA is present in the aqueous solution in a concentration of from about 5 wt % to about 99 wt %. Preferably, the dehydration step occurs at a temperature of from about 200° C. to about 500° C. (more preferably 275° C. to about 450° C.) and a pressure of from about 1 atm to about 5 atm.

The hydration step (DHP to 2-HY-THP) occurs in the presence of water and in the absence of any catalyst or added homogenous acid. Preferably the hydration step occurs and at a temperature of from about 20° C. to about 200° C., more preferably 20° C. to about 150° C. The DHP is preferably present with the water in a concentration of from about 5 wt % to about 80 wt %.

The ring-opening reaction of 2-HY-THP to 1,5-PD is preferably accomplished by contacting the 2-HY-THP with a catalyst comprising a metal selected from the group consisting of Ti, V, Fe, Co, Ni, Cu, Mo, Ru, Rh, Pd, Ag, Re, Ir, Pt, Au and combinations thereof, for a time and at a temperature sufficient to yield 1,5-PD. Many of these catalysts result in essentially quantitative yield of 1,5-PD from 2-HY-THP. Preferred catalysts are NiMo, NiRe, NiV, NiTi, Ni, Fe, Co, Rh, RhRe, RhMo, Pt and PtMo. The selected catalyst(s) may be optionally deposited on a support, such as a carbon or metal-oxide support.

Thus, a more specific version of the method comprises dehydrating tetrahydrofurfural alcohol (THFA) to dihydropyran (DHP) by contacting the THFA with a solid acid catalyst at a temperature of from about 200° C. to about 500° C., and a pressure of from about 1 atm to about 5 atm; hydrating at least a portion of the DHP to 2-hydroxytetrahydropyran (2-HY-THP) in the absence of homogeneous acid at a temperature of from about 20° C. to about 200° C.; and hydrogenating at least a portion of the 2-HY-THP to 1,5-pentanediol by contacting the 2-HY-THP with a catalyst comprising a metal selected from the group consisting of Ti, V, Fe, Co, Ni, Cu, Mo, Ru, Rh, Pd, Ag, Re, Ir, Pt, Au and combinations thereof. The various catalyst and supports noted previously may be used.

It is preferred, but not required, that the entire method be performed in the absence of any noble metal-containing catalyst or reagent.

DETAILED DESCRIPTION

Abbreviations and Definitions

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass. Glucose and HMF for use in the disclosed method may be biomass-derived.

Brønsted-Lowry Acid/Base=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers (($C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose.

"Dehydration catalyst" means any catalyst, without limitation, whether now known or developed in the future, capable of removing water from organic compounds.

"Glucose-containing oligomers, glucose-containing polymers, Glucose-containing reactant, C6-containing reactant"=Any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like.

Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net ($^-3$) charge, and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"Homogeneous catalyst"=A catalyst that exists in the same phase (solid, liquid, or gas) as the reactants under reaction conditions. "Heterogeneous catalyst"=A catalyst that exists in a different phase than the reactants under reaction conditions.

"Hydrofuran" is used herein to refer to any unsubstituted or substituted cyclic ether having a single oxygen heteroatom in the ring, and having five total atoms in the ring and which is derived from furanic compounds. Hydrofurans that are miscible in water, such as tetrahydrofuran (THF), are more appropriate for use in the monophasic reactions described herein. In the biphasic reactions, any hydrofuran may be used.

"Hydropyran" is used herein to refer to any unsubstituted or substituted cyclic ether having a single oxygen heteroatom in the ring, and having six total atoms in the ring and which is derived from pyranic compounds. Hydropyrans miscible in water are more appropriate for use in the monophasic reactions described herein. In the biphasic reactions, any hydropyran may be used.

1,5-PD=1,5-pentanediol. 2-HY-THP=2-hydroxy-tetrahydropyran. 5-HP=5-hydroxypentanal. DHP=dihydropyran. HMF=5-hydroxymethylfurfural. SMSI=strong metal-support interaction. THFA=tetrahydrofurfuryl alcohol. Mineral acid=any mineral-containing acid, including (by way of example and not limitation), hydrochloric acid, nitric acid, phosphoric acid, SA, boric acid, hydrofluoric acid, hydrobromic acid, and the like. WHSV=reactant weight hourly space velocity.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a pseudohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a pseudohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a pseudohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a pseudohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a pseudohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to C2 alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a pseudohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a pseudohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

"Noble metal" is used herein to include ruthenium, rhodium, palladium, silver, osmium, iridium, platinum, gold, and rhenium. Other corrosion-resistant metals that can be used as catalysts in the subject process include titanium, niobium, and tantalum.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Supports for metal catalysts can be any suitable support (now known or developed in the future) that is sufficiently robust to withstand the reaction conditions disclosed herein. Suitable catalyst supports include, by way of example and not limitation, alumina, carbon, ceria, magnesia, niobia, silica, titania, zirconia, zeolites (preferably, Y, ZSM 5, MWW and beta), hydrotalcite, molecular sieves, clays, iron oxide, silicon carbide, aluminosilicates, and modifications, mixtures or combinations thereof.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

The Method:

The method proceeds in three steps:

(1) dehydrating tetrahydrofurfural alcohol (THFA) to dihydropyran (DHP);

(2) hydrating at least a portion of the DHP to 2-hydroxy-tetrahydropyran (2-HY-THP) in the absence of homogeneous acid; and

(3) hydrogenating at least a portion of the 2-HY-THP to 1,5-pentanediol.

Step 1, the THFA dehydration, preferably occurs over a solid acid catalyst as defined above. Preferred is a $\gamma\text{-Al}_2\text{O}_3$ catalyst, which afforded >93% yield to DHP Step 2, the DHP hydration, does not require any catalyst, nor does it require added homogenous acid. It takes place in water and afforded approximately 94% yield to 2-HY-THP Step 3, the 2-HY-THP hydrogenolysis was substantially quantitative when NiMo/carbon was used as the catalyst; the reaction afforded ~100% yield to 1,5-PD.

The overall three-step process (from THFA) is depicted below:

The preliminary hydrogenation of furfural to THFA shown above is not part of the present process, but indicates a preferred source for the THFA reactant.

A huge benefit of the method is its overall costs, which is vastly cheaper than conventional routes that require using noble metal catalyst. Table 1 is a brief comparison of the cost of the catalysts typically used in the conventional dehydration route to 1,5-PD, versus the cost of the catalysts used in the current method.

TABLE 1

Comparative Cost of Catalysts

| Catalysts used in conventional route to 1,5-PD | Price ($/kg, 2014) | Preferred catalysts used in present method | Price ($/kg, 2014) |
| --- | --- | --- | --- |
| Rh | $38,000 | $\gamma\text{-Al}_2\text{O}_3$ | <$1 |
| Ir | $18,000 | NiMo/Carbon | Ni: $17 |
| Pt | $46,000 |  | Mo: $27 |
| Re | $ 3,000 | Co/TiO$_2$ | Co: $31 |
|  |  |  | TiO$_2$: <$1 |

As shown in Table 1, the present method yield 1,5-PD at a catalyst cost that is roughly 10,000-fold less than the catalyst cost of the conventional route. We have estimated that production costs (in 2014 dollars) for producing 1,5-PD by hydrogenolysis of THFA using a noble metal catalyst is approximately $582/ton 1,5-PD. This corresponds to an economic potential of −$281/ton 1,5-PD for this route.

In contrast, the present method does not utilize noble metal catalysts and thus has a much lower production cost. It also operates at higher reactant concentrations, so energy costs relating to product distillation are slashed as well. In contrast to the hydrogenolysis of THFA route, 1,5-PD can be produced via the present method for an estimated cost of approximately $77/ton. This corresponds to an economic potential of +$439/ton 1,5-PD. In short, the present route represents an immense upgrade from the THFA hydrogenolysis route economically.

Moreover, the present method, despite its greatly reduced costs, results in improved yields. For example, Table 2 compares the requirements and yields of the present method versus the route described by Schniepp and Geller (August 1946) *J. Amer. Chem. Soc.* 68(8):1646-1648.

TABLE 2

Requirements and yields as compared to Schniepp and Geller (1946)

| | Criteria | Schniepp and Geller (1946) | Huber/Dumesic (2015) |
| --- | --- | --- | --- |
| Step 1: THFA Dehydration | Feed | 100% THFA vapor | 100% THFA vapor |
| | Catalyst | $\gamma\text{-Al}_2\text{O}_3$ | $\gamma\text{-Al}_2\text{O}_3$ |
| | Yield | 89% | >93% |
| Step 2: DHP Hydration | Feed | 20% DHP/H$_2$O | 50% DHP/H$_2$O |
| | Catalyst | 0.2N HCl | None |
| | Yield | 78% 5-hydroxy pentanal | 94% 2-HY-THP |
| Step 3: 1,5-PD Formation | Feed | 5-hydroxy pentanal | 2-HY-THP |
| | Catalyst | Copper-chromite | NiMo/C |
| | Yield | ~100% | ~100% |
| Step Integration | Step 2 + Step 3 Yield | 61% | 94% |
| | Overall Yield (sum of separate steps) | 70% | >90% |

In short, as compared to the Schniepp and Geller approach, overall yield in the present method increased from ~70% to >90%. Additionally, in the present method there is no need for a mineral acid catalyst (HCl) in DHP hydration step. Omitting the need for a mineral acid catalyst also does away with the additional step of neutralizing the acid prior to the next step in the method. This eliminates a difficult and costly separation/neutralization of homogeneous acid.

A number of catalysts give 100% yields to 1,5-PD from 2-HY-THP. Among these catalysts are NiMo, NiRe, NiV, NiTi, Ni, Fe, Co, Rh, RhRe, RhMo, Pt, and PtMo.

Table 3 shows the results for continuous flow reactions after 12 hours time on stream when using various solid acid catalysts for the first step, dehydration of THFA to DHP:

Tetrahydrofurfuryl Alcohol (THFA)    Dihydropyran (DHP)

TABLE 3

Vapor-Phase THFA Dehydration: Acid Catalysts

| Catalyst | Mass of Catalyst (mg) | Rxn Temp (° C.) | Pressure (atm) | Reactant (wt %) | Solvent (wt %) | Conversion (%) | Selectivity to DHP (%) | Selectivity to Unknown Products (%) |
|---|---|---|---|---|---|---|---|---|
| γ-Al$_2$O$_3$ | 150 | 375 | 1 | THFA-100% | N/A | 100 | 93 | 0.5 |
| Silica Alumina | 25 | 350 | 1 | THFA-20% | MeOH-80% | 95 | 46 | 10 |
| ZrO$_2$ | 130 | 375 | 1 | THFA-100% | N/A | 40 | 80 | 6 |

Table 4 depicts the results of the hydration reaction, DHP to 2-HY-THP:

Dihydropyran (DHP)

2-Hydroxytetrahydropyran (2-HY-THP)    5-Hydroxypentanal (5-HP)

TABLE 4

DHP to 2-HY-THP

| Catalyst | Reaction Temp (° C.) | Reaction Time (hr) | Reactant (wt %) | Solvent (wt %) | Conversion (%) | Selectivity to 2-HY-THP (%) |
|---|---|---|---|---|---|---|
| N/A | 70 | 12 | DHP-50% | H$_2$O-50% | 100 | 94 |

As shown in Table 4, the DHP can be converted into 2-HY-THP in very high yields (94%). This step represents a departure from the Schniepp and Geller (1946) approach, which seeks to maximize the production of 5-hydroxypentanal (78%; see Table 2), rather than 2-HY-THP as in the present method (94%; see Table 4). Schniepp and Geller fail to recognize that the 2-HY-THP can be maximized more than the yield to 5-hydroxypentanal. Because the final ring-opening step is substantially quantitative the overall yield of the present method is much improved as compared to the Schniepp and Geller route. In the present approach, the two typically are not separated (although that is an option). Separation by distillation or any other means simply is not required because purification of the intermediate is not necessary to quantitatively produce 1,5-PD, in contract to the Schniepp and Geller route.

As shown in Tables 5A and 5B, the final step, 2-HY-THP to 1,5-PD, is substantially quantitative using a number of different base metal and noble metal catalysts:

2-Hydroxytetrahydropyran (2-HY-THP)    1,5-Pentanediol (1,5-PDO)

TABLE 5A

2-HY-THP Results: Catalyst Screening

| Catalyst | Mass Catalyst (g) | Reaction Time (min) | Conversion (%) | Rate of Formation of 1,5-PD (μmol/(min*gcat)) | Selectivity to 1,5-PD (%) |
|---|---|---|---|---|---|
| 1:1 NiMo/C | 0.001 | 60 | 22.5 | 8916 | 100.0% |
| 1:0.5 NiMo/SiO$_2$ | 0.001 | 60 | 15.8 | 6359 | 100.0% |
| 1:0.2 NiRe/C | 0.001 | 60 | 16 | 5505 | 100.0% |
| 1:0.25 NiMo/C | 0.001 | 60 | 8.7 | 4075 | 100.0% |
| 1:0.25 NiW/SiO$_2$ | 0.001 | 60 | 11.2 | 4014 | 100.0% |
| 1:0.1 NiMo/C | 0.001 | 60 | 6.4 | 2465 | 100.0% |
| 1:0.1 NiV/SiO$_2$ | 0.001 | 60 | 7.4 | 2305 | 94.5% |
| 1:0.5 NiNb/SiO$_2$ | 0.001 | 60 | 4.9 | 1213 | 77.2% |
| 1:0.5 NiTi/SiO$_2$ | 0.001 | 60 | 3.7 | 2057 | 100.0% |
| Pt/C | 0.0056 | 180 | 30.7 | 748 | 100.0% |
| Ni/SiO$_2$ | 0.0098 | 60 | 6.3 | 574 | 100.0% |
| Rh/C | 0.0055 | 180 | 21.8 | 508 | 100.0% |
| Co/SiO$_2$ | 0.0257 | 240 | 10.5 | 37 | 99.7% |
| FePK/Al2O3 | 0.0263 | 180 | 4.5 | 31 | 100.0% |
| 1:0.1 RhMo/C | 0.005 | 60 | 99* | 7700 | 100.0% |
| 1:1RhRe/C | 0.005 | 60 | 99* | 7700 | 100.0% |
| BASF Cu | 0.0251 | 360 | 75* | 153 | 88.0% |

TABLE 5B

2-HY-THP Results: Catalyst Screening (More)

| Catalyst | Rate per gram Metal (μmol/ (min*g metal)) | Rate per Total Parent Metal Sites (1/s) | Rate per Parent Metal Surface Sites (1/s) |
| --- | --- | --- | --- |
| 1:1 NiMo/C | 297,200 | 0.29 | 4.95 |
| 1:0.5 NiMo/SiO$_2$ | 211,967 | 0.21 | 3.53 |
| 1:0.2 NiRe/C | 183,500 | 0.18 | 3.06 |
| 1:0.25 NiMo/C | 135,833 | 0.13 | 2.26 |
| 1:0.25 NiW/SiO$_2$ | 133,800 | 0.13 | 2.23 |
| 1:0.1 NiMo/C | 82,167 | 0.08 | 1.37 |
| 1:0.1 NiV/SiO$_2$ | 76,833 | 0.08 | 1.28 |
| 1:0.5 NiNb/SiO$_2$ | 40,433 | 0.04 | 0.67 |
| 1:0.5 NiTi/SiO$_2$ | 68,567 | 0.07 | 1.14 |
| Pt/C | 18,700 | 0.06 | |
| Ni/SiO$_2$ | 19,133 | 0.02 | 0.32 |
| Rh/C | 12,700 | 0.02 | 0.07 |
| Co/SiO$_2$ | 740 | 0.001 | |
| FePK/Al2O$_3$ | 361 | 0.00 | |
| 1:0.1 RhMo/C | 192,500 | 0.33 | |
| 1:1RhRe/C | 192,500 | 0.33 | |
| BASF Cu | 306 | 0.0003 | |

Reaction conditions: T = 120° C., P = 950 psi H$_2$, (64.6 atm), 1 wt % 2-HY-THP/H$_2$O Based on the low conversion results presented in Tables 5A and 5B, additional high conversion reactions were studied for the 2-HY-THP to 1,5-PD hydrogenolysis reaction. See Table 6.

TABLE 6

Catalyst Screening: High-Conversion Reactions

| Catalyst | Conversion (%) | Selectivity to 1,5-PD (%)* | Selectivity to 1,5-PD based on product area (assumes same sensitivity):* |
| --- | --- | --- | --- |
| Cu/Al$_2$O$_3$ | 75.1 | 88.7% | 79.3% |
| Ni/SiO$_2$ | 99.1 | 100.0% | 94.2% |
| Ni/SiO$_2$ | 94.2 | 100.0% | 87.1% |
| Ni/SiO$_2$ | 73.1 | 100.0% | 97.5% |
| 1:0.5 NiMo/SiO$_2$ | 99.8 | 100.0% | 96.4% |
| 1:0.5 NiMo/SiO$_2$ | 85.3 | 100.0% | 97.9% |
| 1:0.5 NiNb/SiO$_2$ | 98.1 | 100.0% | 97.0% |
| 1:0.5 NiTi/SiO$_2$ | 99.3 | 100.0% | 90.5% |
| 1:0.1 NiV/SiO$_2$ | 99.3 | 100.0% | 89.0% |
| 1:0.25 NiW/SiO$_2$ | 99.4 | 100.0% | 94.7% |
| 1:0.15 PtMo/C | 69.2 | 98.0% | 90.8% |
| 1:0.1 RhMo/C | 99.5 | 100.0% | 96.5% |
| 1:0.1 RhMo/C | 97.5 | 100.0% | 97.2% |
| 1:0.1 RhMo/C | 86.2 | 100.0% | 92.8% |
| 1:1 RhRe/C | 99.6 | 100.0% | 98.3% |
| 1:1 RhRe/C | 98.0 | 100.0% | 96.4% |
| 1:1 RhRe/C | 97.2 | 100.0% | 94.3% |

Reaction Conditions: T = 120° C., P = 950 psi H$_2$, 1 wt % 2-HY-THP/H$_2$O
*The sensitivities showed that the selectivity to 1,5-PD was 100%. There was an additional small peak for nickel catalysts which is why the selectivities have also been calculated based on the areas.

Figure 1:
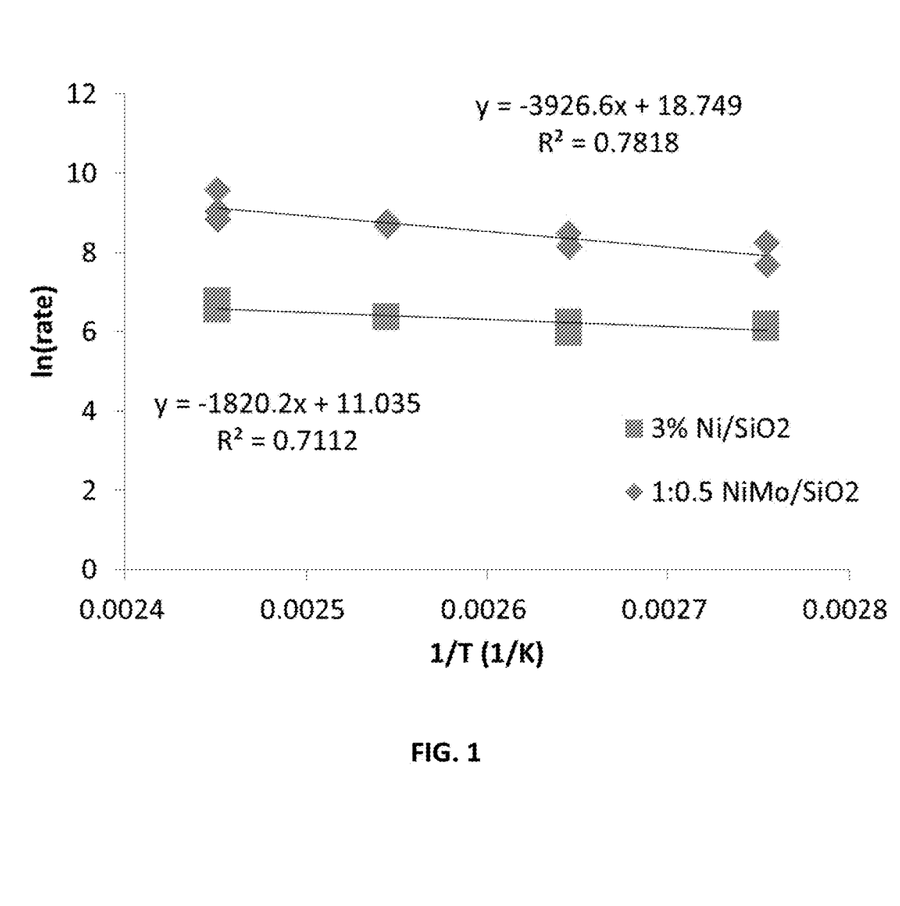
FIG. 1 is a graph depicting the results of activation energy studies for Ni and NiMo catalysts from 90° C. to 135° C. ■=3% Ni/SO$_2$. ♦=1.0:0.5 NiMo/SiO$_2$.

Turning to the figures, FIG. 1 is a graph depicting the results of activation energy studies for Ni and NiMo catalysts from 90° C. to 135° C. ■=3% Ni/SO$_2$. ◆=1.0:0.5 NiMo/SiO$_2$. The activation energy for the hydrogenolysis of 2-HY-THP using a Ni catalyst was calculated to be 15.1+/−9.6 kJ/mol; while the corresponding value when using NiMo was calculated to be 32.6+/−15.4 kJ/mol. While not being limited to any specific underlying phenomenon or mechanism, the substantial difference in the reaction rate when using these two catalysts must be a function of the entropy of formation of the transition state.

Figure 2:
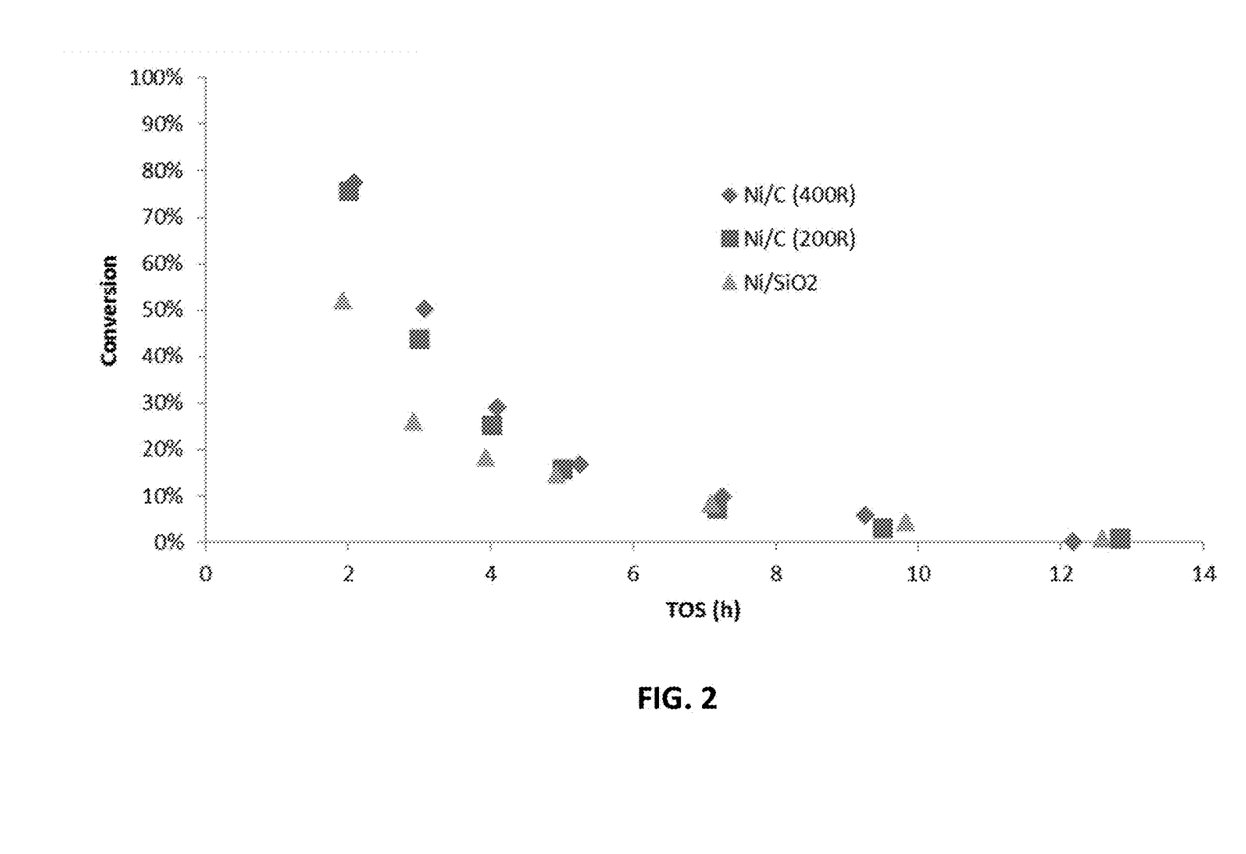
FIG. 2 is a graph depicting catalyst stability. Conversion percent is shown on the Y-axis; time-on-stream (TOS) in hours is shown on the X-axis. ■=Ni/C (200 R). ♦=Ni/C (400 R). ▲=Ni/SiO$_2$.

FIG. 2 is a graph depicting catalyst stability. Conversion percent is shown on the Y-axis; time-on-stream (TOS) in hours is shown on the X-axis. ■=Ni/C (200 R). ◆=Ni/C (400 R). ▲=Ni/SiO$_2$. Carbon and silica-supported Ni are not overly stable at a reduction temperature of 200° C. and did not show improved results when a higher reduction temperature of 400° C. was used. Co—TiO2 (20 wt % 2-HY-THP in flow reactor) showed a strong metal-support interaction resulting in 100% yields to 1,5-PD observed.

Figure 3:
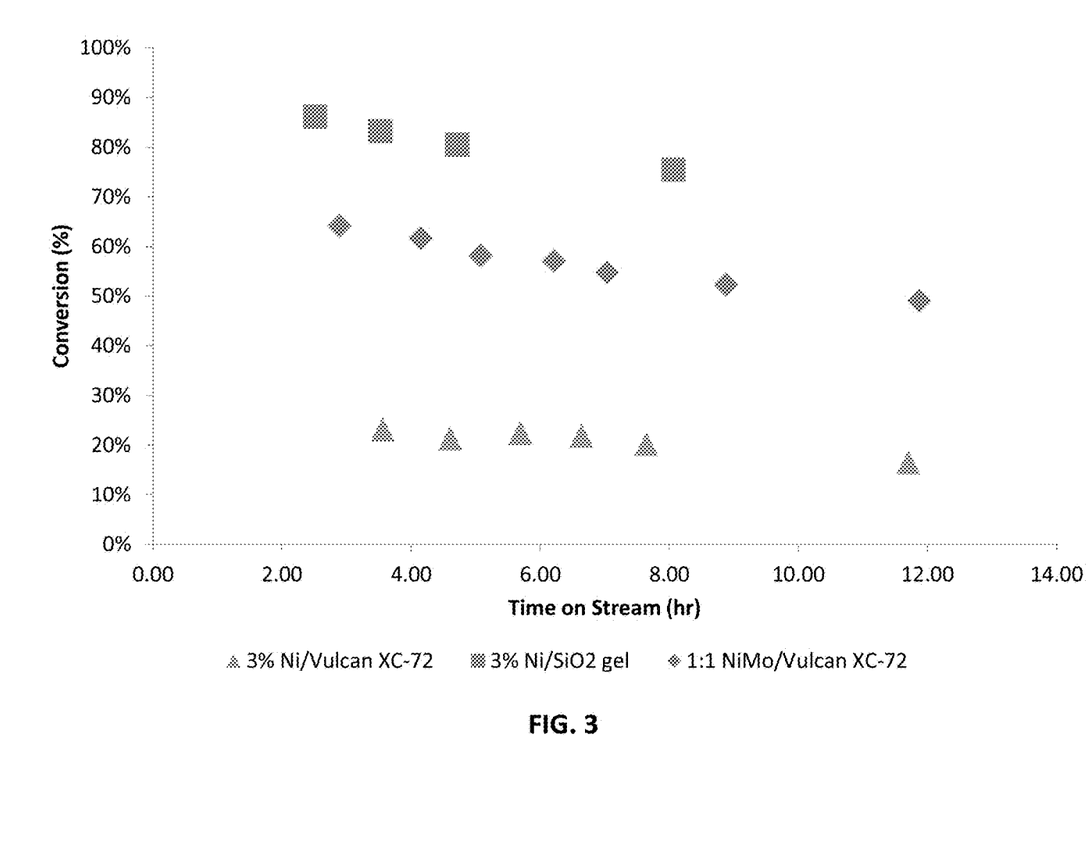
FIG. 3 is a graph depicting catalyst stability. Conversion percent is shown on the Y-axis; time-on-stream (TOS) in hours is shown on the X-axis. ■=3% Ni/SiO$_2$. ♦=1:1 NiMo/Vulcan Carbon (105° C.) ▲=3% Ni/Vulcan Carbon (120° C.).

FIG. 3 is another graph depicting catalyst stability. Conversion percent is shown on the Y-axis; time-on-stream (TOS) in hours is shown on the X-axis. ■=3% Ni/SiO$_2$. ◆=1:1 NiMo/Vulcan Carbon (105° C.) ▲=3% Ni/Vulcan Carbon (120° C.). A reduction temperature of 550° C. improved the stability of Ni/C catalysts. During the reduction step, the temperature was ramped to 550° C. over the course 6 hours and then held steady for 2 hours at 550° C. The rates at the first stable drain (μmol/min/g catalyst) were:
3% Ni/C: 59
3% Ni/SiO$_2$: 230
1:1 NiMo/C: 4250
The reaction conditions for Ni were: T=120° C., P=700 psi H$_2$, 1 wt % 2-HY-THP/H$_2$O, WHSV=1.6 h$^{-1}$. The reaction conditions for NiMo were: T=105° C., P=700 psi H$_2$, 1 wt % 2-HY-THP/H$_2$O, WHSV=40.7 h$^{-1}$.

Figure 4:
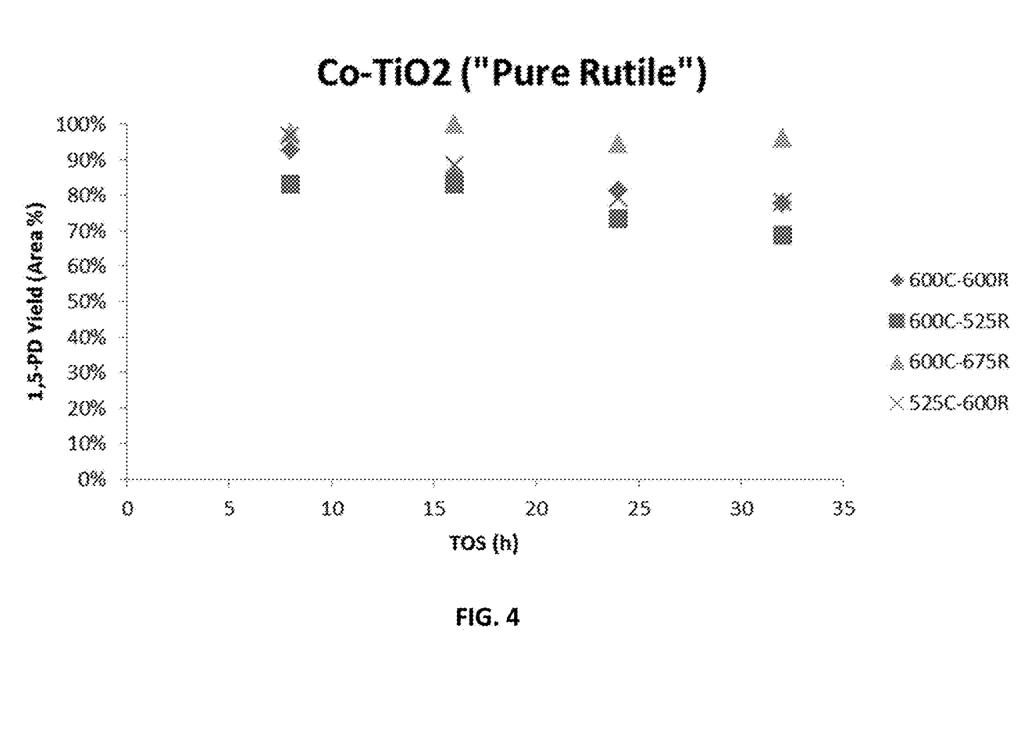
FIG. 4 is a graph depicting catalyst stability of a Co—TiO$_2$ catalyst (TiO$_2$ pre-calcined at 750° C.) at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ♦=600 C-600 R. ■=600 C-525 C. ▲=600 C-675 R. X=525 C-600 R.

FIG. 4 is a graph depicting catalyst stability of a Co—TiO2 catalyst at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ◆=600 C-600 R. ■=600 C-525 C. ▲=600 C-675 R. X=525 C-600 R. The Co—TiO$_2$ was synthesized by impregnation of Co onto pure rutile TiO$_2$ support (calcined before impregnation at 750° C.) up to 5 wt % Co. The reaction conditions for all catalysts were: T=120° C., P=650 psi H$_2$, 1 wt % 2-HY-THP/H$_2$O, WHSV=0.95 h$^{-1}$.

Figure 5:
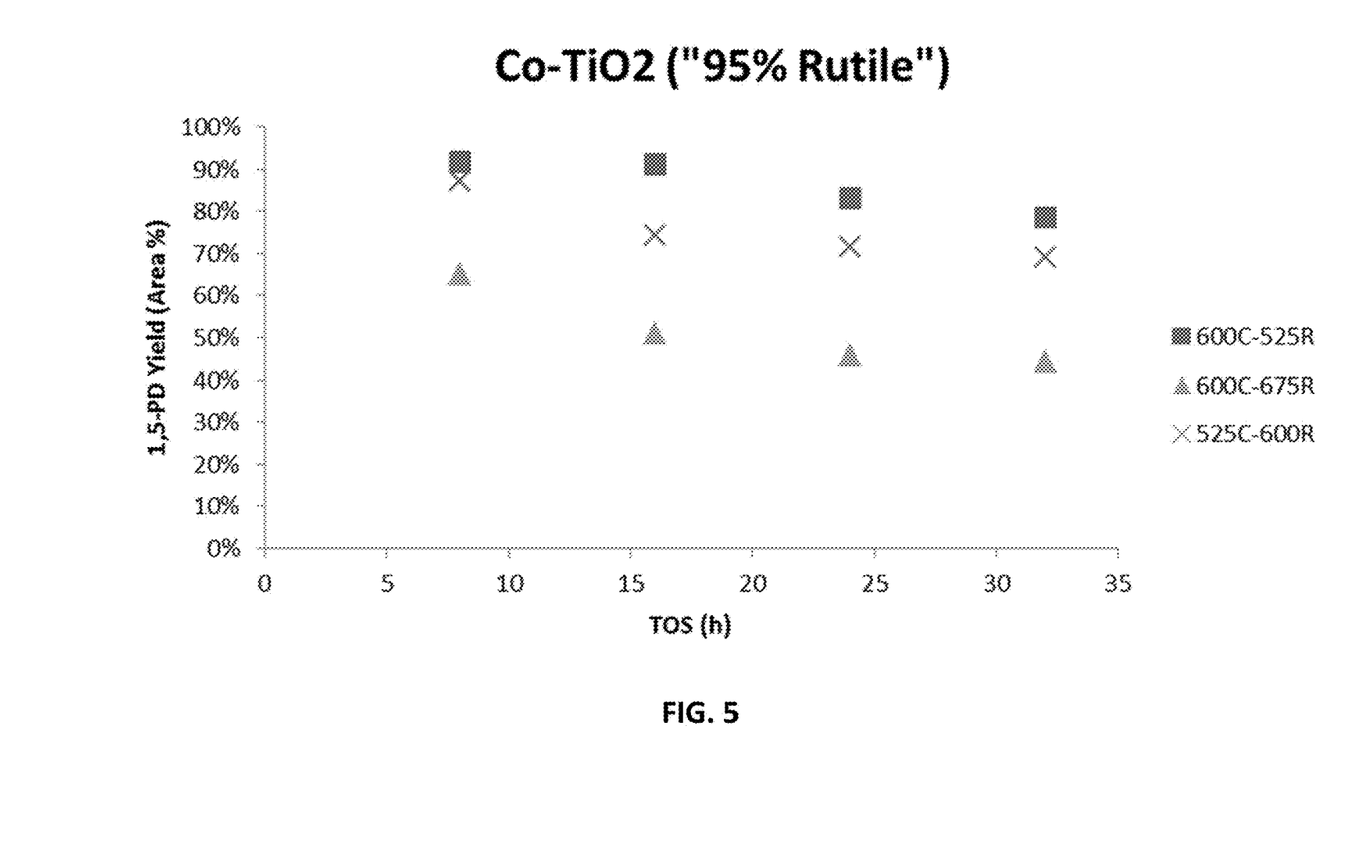
FIG. 5 is a graph depicting catalyst stability of a Co—TiO2 catalyst (TiO$_2$ pre-calcined at 700° C.) at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ■=600 C-525 C. ▲=600 C-675 R. X=525 C-600 R.
Figure 6:
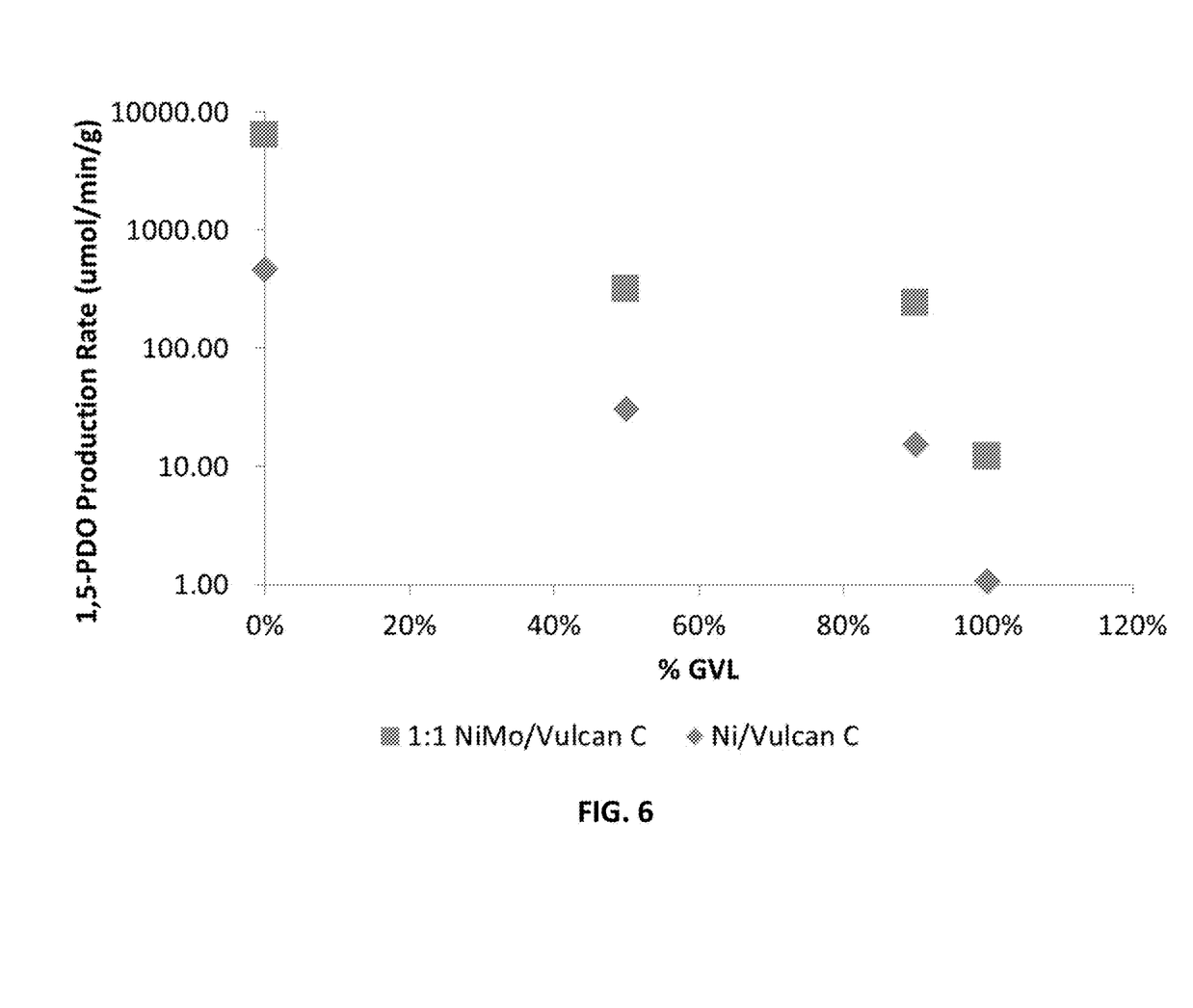
FIG. 6 is a graph depicting the effect of varying the concentration of GVL on hydrogenolysis. ▲=3% Ni/Vulcan Carbon (120° C.). ■=3% Ni/SiO$_2$ (120° C.).

FIG. 5 is a graph depicting catalyst stability of a Co—TiO$_2$ catalyst at different pretreatment temperatures. 1,5-PD yield percentage is shown on the Y-axis; time-on-stream (TOS) in hours is shown on the X-axis. The pretreatment consisted of a calcination ('C') followed by a reduction ('R') with the temperatures of each given in degrees Celsius. ■=600 C-525 C. ▲=600 C-675 R. X=525 C-600 R. The Co—TiO$_2$ was synthesized by impregnation of Co onto an approximately 95% rutile/5% anatase TiO$_2$ support (calcined before impregnation at 700° C.) up to 5 wt % Co. The reaction conditions for all catalysts were: T=120° C., P=650 psi H$_2$, 1 wt % 2-HY-THP/H$_2$O, WHSV=0.95 h$^{-1}$. FIG. 6 is a graph depicting the effect of varying the concentration of gamma-valerolactone (GVL) on hydrogenolysis. ▲=3% Ni/Vulcan Carbon (120° C.). ■=3% Ni/SiO$_2$ (120° C.). FIG. 6 shows that reaction rates are drastically reduced in a water and polar aprotic solvent mixture. The reaction conditions were: T=120° C., P=950 psi H$_2$, 1 wt % 2-HY-THP/H$_2$O.

Figure 7:
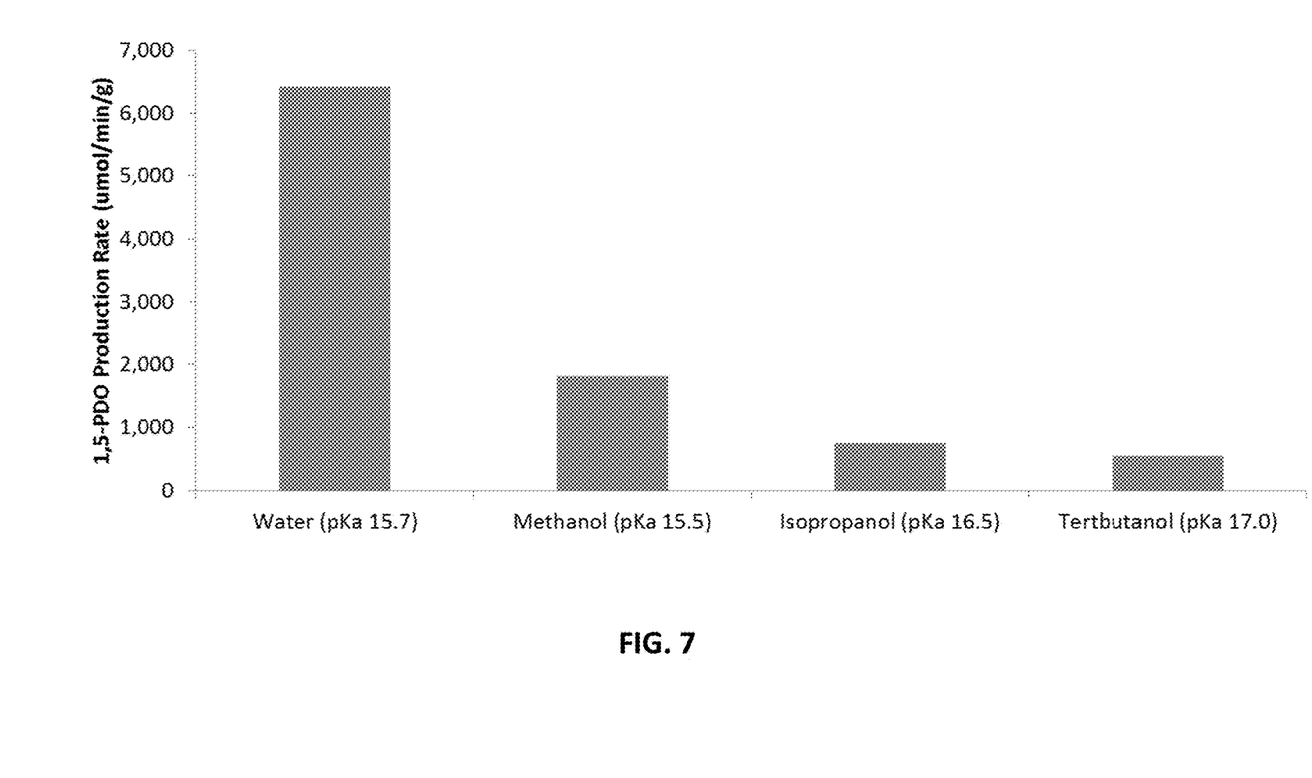
FIG. 7 is a histogram depicting the effect of solvent selection on hydrogenolysis rates.

FIG. 7 is a histogram depicting the effect of solvent selection on hydrogenolysis rates. As shown in the figure, water works best among the solvents tested, but primary, secondary, and/or tertiary short-chain alcohols may also be used as solvents. The reaction conditions were: T=120° C., P=950 psi H$_2$, 1 wt % 2-HY-THP.

Figure 8:
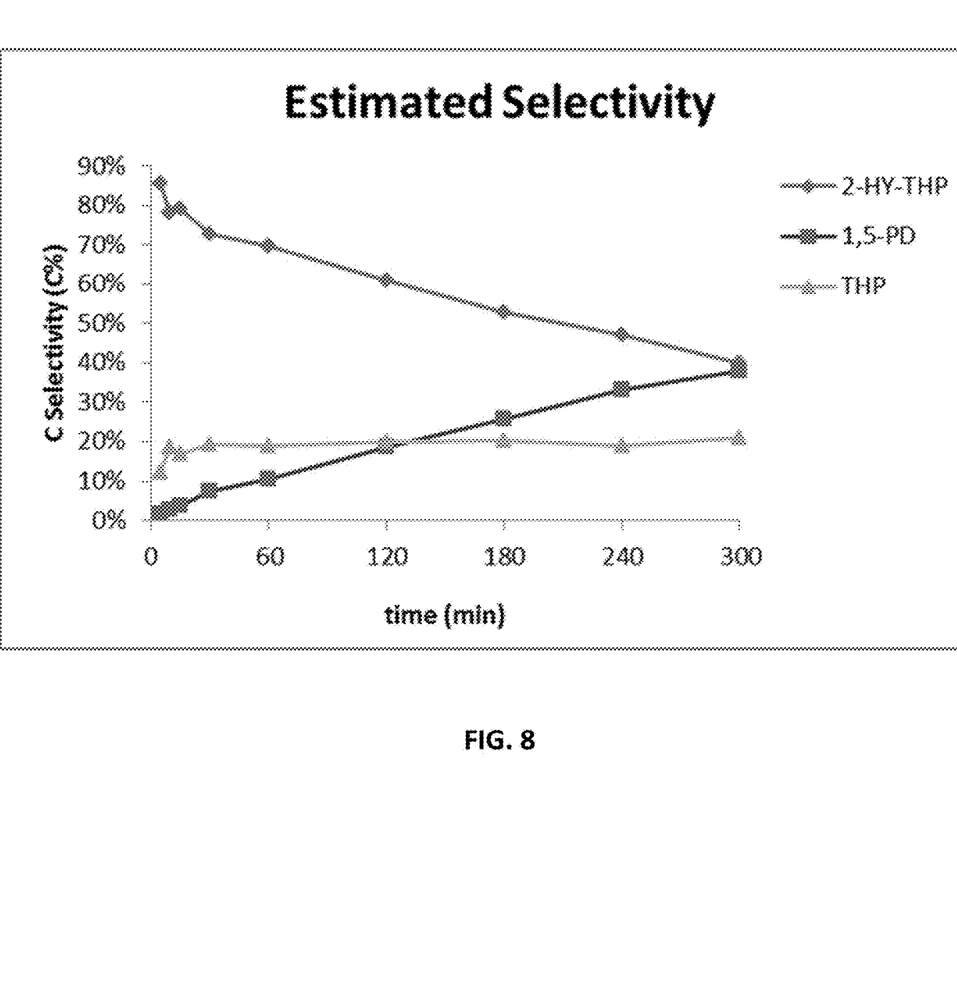
FIG. 8 is a graph depicting product selectivity results for a one-pot hydration-hydrogenolysis reaction of 20 wt % DHP/H$_2$O over a RhRe/C catalyst at 120° C. for 4 h. ♦=2-HY-THP. ■=1,5-PD. ▲=THP.

FIG. 8 is a graph depicting estimated product selectivity results for a one-pot hydration-hydrogenolysis reaction of 20 wt % DHP/H$_2$O over a RhRe/C catalyst at 120° C. for 4 h. ◆=2-HY-THP. ■=1,5-PD. ▲=THP. The reaction conditions were 20 wt % DHP/H$_2$O over a RhRe/C catalyst at 120° C. for 4 hours in a Parr reactor. Selectivity was based on product selectivity (rather than reactant conversion) because the data for DHP are unreliable due to its limited solubility in water. As shown in the figure, DHP converts to 2-HY-THP and THP at reaction onset, while the production of 1,5-PD is essentially linear over the time course of the experiment.

Figure 9:
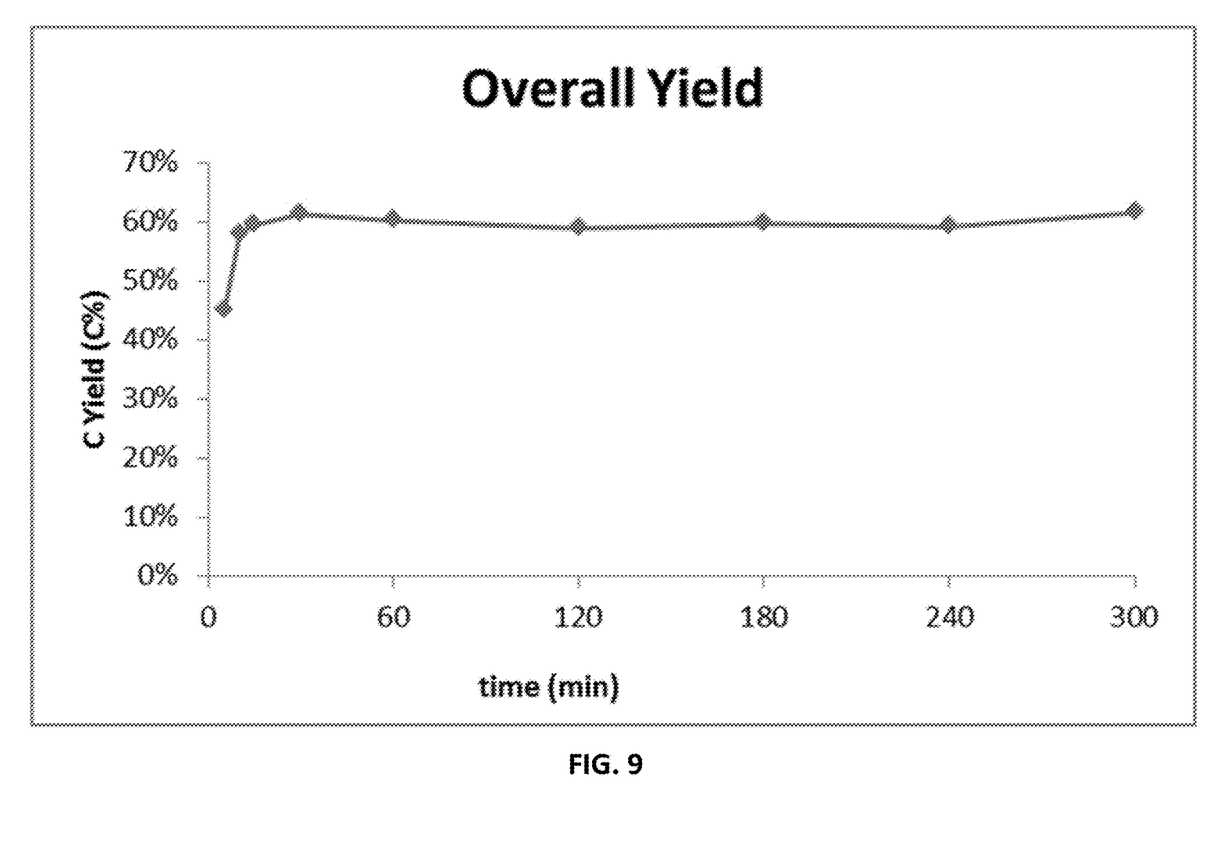
FIG. 9 is a graph depicting overall yield results for a one-pot hydration-hydrogenolysis reaction of 20 wt % DHP/H$_2$O over a RhRe/C catalyst at 120° C. for 4 h.

FIG. 9 is a graph depicting overall yield results for a one-pot hydration-hydrogenolysis reaction of 20 wt % DHP/$H_2O$ over a RhRe/C catalyst at 120° C. for 4 h. The absolute yield in this particular experiment, and shown in FIG. 9, is low due to a calibration error in the gas chromatograph used. However, the graph shows that the ultimate yield is reached early in the run (well under 60 min) and remains steady throughout the 300 min reaction.

What is claimed is:

1. A method of making 1,5-pentanediol, the method comprising:
   (a) dehydrating tetrahydrofurfural alcohol (THFA) to dihydropyran (DHP);
   (b) hydrating at least a portion of the DHP to 2-hydroxytetrahydropyran (2-HY-THP) in the absence of homogeneous acid; and
   (c) hydrogenating at least a portion of the 2-HY-THP to 1,5-pentanediol.

2. The method of claim 1, wherein step (a) comprises dehydrating the THFA by contacting it with a solid acid catalyst.

3. The method of claim 2, wherein the solid acid catalyst is selected from the group consisting of solid Brønsted acid catalysts, solid Lewis acid catalysts, and combinations thereof.

4. The method of claim 1, wherein step (a) occurs on neat THFA or on an aqueous solution of THFA and the THFA is present in the aqueous solution in a concentration of from about 5 wt % to about 99 wt %.

5. The method of claim 4, wherein step (a) occurs at a temperature of from about 200° C. to about 500° C. and a pressure of from about 1 atm to about 5 atm.

6. The method of claim 5, wherein step (a) occurs at a temperature of from about 275° C. to about 450° C.

7. The method of claim 1, wherein step (b) occurs in the presence of water and at a temperature of from about 20° C. to about 200° C.

8. The method of claim 7, wherein the DHP is present with the water in a concentration of from about 5 wt % to about 80 wt %.

9. The method of claim 8, wherein step (b) occurs at a temperature of from about 20° C. to about 150° C.

10. The method of claim 1, wherein in step (c), at least a portion of the 2-HY-THP is hydrogenated to 1,5-pentanediol by contacting the 2-HY-THP with a catalyst comprising a metal selected from the group consisting of Ti, V, Fe, Co, Cu, Ni, Mo, Rh, Ru, Pd, Au, Ag, Jr, Re, Pt, and combinations thereof.

11. The method of claim 10, wherein in step (c), at least a portion of the 2-HY-THP is hydrogenated to 1,5-pentanediol by contacting the 2-HY-THP with a catalyst selected from the group consisting of NiMo, NiRe, NiV, NiTi, Ni, Fe, Co, Rh, RhRe, RhMo, Pt and PtMo.

12. The method of claim 10, wherein the catalyst is deposited on a support.

13. The method of claim 12, wherein the support is selected from the group consisting of carbon and metal oxides.

14. A method of making 1,5-pentanediol, the method comprising:
   (a) dehydrating tetrahydrofurfural alcohol (THFA) to dihydropyran (DHP) by contacting the THFA with a solid acid catalyst at a temperature of from about 200° C. to about 500° C., and a pressure of from about 1 atm to about 5 atm;
   (b) hydrating at least a portion of the DHP to 2-hydroxytetrahydropyran (2-HY-THP) in the absence of homogeneous acid at a temperature of from about 20° C. to about 200° C.; and
   (c) hydrogenating at least a portion of the 2-HY-THP to 1,5-pentanediol by contacting the 2-HY-THP with a catalyst comprising a metal selected from the group consisting of Ti, V, Fe, Co, Cu, Ni, Mo, Rh, Ru, Pd, Au, Ag, Jr, Re, Pt, and combinations thereof.

15. The method of claim 14, wherein in step (c), at least a portion of the 2-HY-THP is hydrogenated to 1,5-pentanediol by contacting the 2-HY-THP with a catalyst selected from the group consisting of NiMo, NiRe, NiV, NiTi, Ni, Fe, Co, Rh, RhRe, RhMo, Pt and PtMo.

16. The method of claim 14, wherein the catalyst is deposited on a support.

17. The method of claim 16, wherein the support is selected from the group consisting of carbon and metal oxides.

18. The method of claim 14, wherein all of steps (a), (b), and (c) are performed in the absence of a noble metal.

* * * * *